United States Patent [19]

Yamamoto et al.

[11] Patent Number: 5,056,228
[45] Date of Patent: Oct. 15, 1991

[54] JIG FOR CROSS HATCHING TEST

[75] Inventors: Norihiko Yamamoto, Toyonaka; Manabu Nakamura, Osaka, both of Japan

[73] Assignee: Taiyu Kizai Co., Ltd., Osaka, Japan

[21] Appl. No.: 588,432

[22] Filed: Sep. 26, 1990

[51] Int. Cl.$^5$ ................................................ B43L 5/00
[52] U.S. Cl. ...................................... 33/1 B; 33/563; 33/494
[58] Field of Search ............... 33/1 B, 1 R, 1 F, 1 K, 33/563, 834, 483, 494, 429; 73/150 R, 150 A

[56] References Cited

U.S. PATENT DOCUMENTS 563,465  7/1896  Farcey ................................. 33/476

FOREIGN PATENT DOCUMENTS

| 520561 | 2/1921 | France | 33/1 B |
| 534141 | 10/1955 | Italy | 33/476 |
| 102477 | 9/1941 | Sweden | 33/476 |

*Primary Examiner*—Harry N. Haroian
*Attorney, Agent, or Firm*—Bryan, Cave, McPheeters & McRoberts

[57] ABSTRACT

A jig for a cross hatching test which is rectangular in shape and is used for ruling straight lines intersecting each other at a predetermined angle on a rectangular test plate, including (a) a first straight line passing on the surface of the jig with an angle, for adjusting the left longer side of the test plate to draw a straight line on the test plate with the right longer side of the jig; (b) a second straight line orthogonal to the first straight line, for adjusting the lower shorter side of the test plate; (c) a third straight line with the predetermined angle to the left longer side of the jig, for adjusting the drawn straight line to draw another straight line with the left longer side of the jib with the predetermined angle to the previously drawn straight line; and (d) an opening interposed in the middle of the first straight line, for adjusting the left longer side of the plate to the first straight line to draw the straight line on the test plate with the right longer side of the jig.

7 Claims, 4 Drawing Sheets

FIG.2
FIG.3
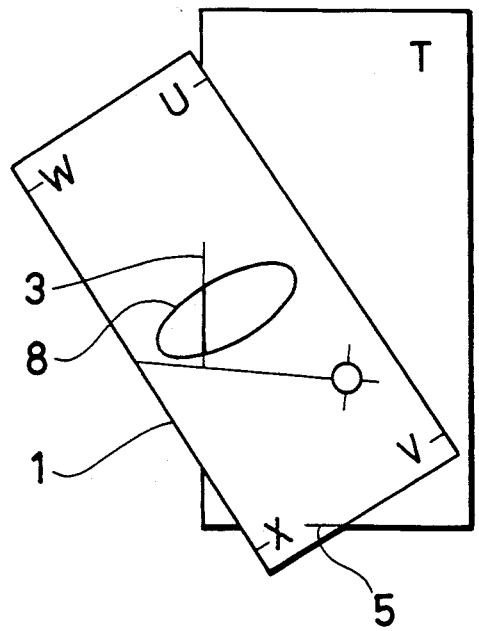
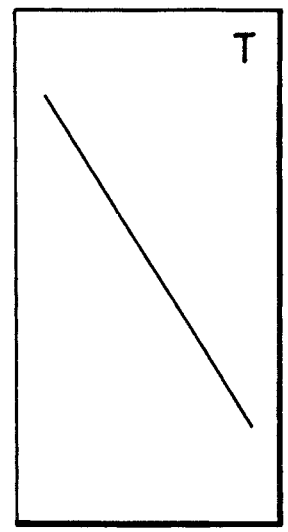
FIG.4
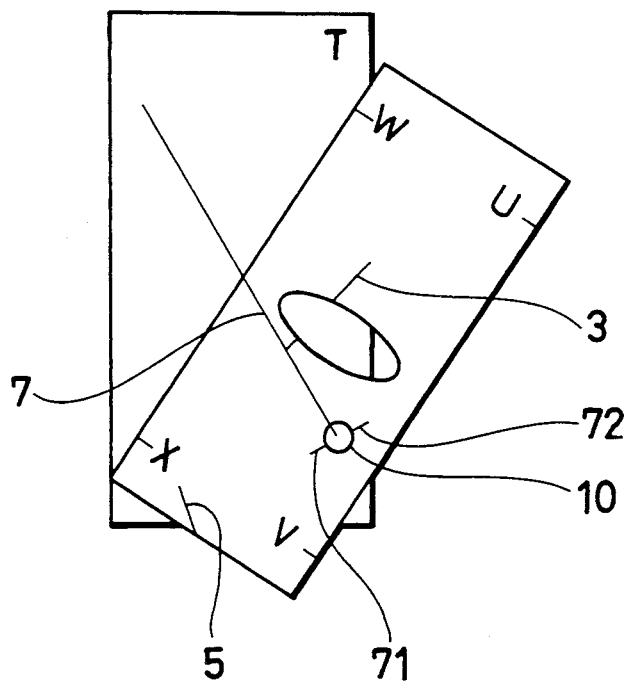

JIG FOR CROSS HATCHING TEST

BACKGROUND OF THE INVENTION

1. Field of the Invention

The present invention is a jig for performing a cross hatching test, and more specifically, it is a jig for performing a cross hatching test which is applied for adhesiveness measurement of all kinds of coating materials such as thin film, ink and the like.

2. Description of the Background Art

A test for checking adhesive strength of thin film, ink and the like (referred to as "paint film" hereinafter) usually includes a cross-cut adhesion test, a salt spray test, etc.

In the cross-cut adhesion test, a paint film is formed on a rectangular sample piece (referred to as "test plate" hereinafter) of predetermined dimensions, and a lattice layout of cuts is made through the paint film up to the base of the test plate with a sharp-edged tool, so that fragility of the paint film and propriety of its adhesiveness to the base may be estimated from flaws extended from the cuts (JIS K 5400). Specifically, a designated strip of adhesive tape or the like is affixed to the paint film which has cuts in it in a lattice layout, and pulled off in a direction orthogonal to the test plate, and then the paint film which has been peeled away is compared with a reference photograph or the like in order to evaluate the adhesive strength by comparing various points of the peeling.

On the other hand, in the salt spray test, a paint film is formed on a test plate similar to that used in the above test, and a cross-cut layout (60°, 30°) of scars is made through the paint film up to the base of the test plate with a sharp-edged tool. The test plate is placed in a device for generating a salt water fog (a device prescribed by JIS Z 2371) for the primary purpose of determining whether the fog of salt water acts on the paint film to make it rusty or swollen (JIS K 5400).

Usually, the above-mentioned two tests are applied to the same paint film at the same time. Thus, it is expedient that a jig for these tests has both slits for making cuts in the cross-cut adhesion test and with lines for making cross-cuts in the salt spray test, on the same plate.

When making the cross-cuts utilizing the jig, it is necessary to position an intersection in the center of the test plate and insure that the cross-cuts are almost uniformly laid out on the test plate. The accuracy of this procedure is always quite dependent upon the perception of the operator.

With the test applied under such circumstances, reproducibility of the cross-cuts declines and the test results suffer due to non-uniformity.

SUMMARY OF THE INVENTION

The present invention is a rectangularly shaped jig used for ruling straight lines intersecting each other at a predetermined angle on a rectangular test plate, for performing a cross hatching test. According to the present invention, the jig comprises:

(a) a first straight line defined on the surface of the jig for alignment with the first longer side of the test plate to orient the jig for cutting a straight line on the test plate along the opposite longer side of the jig;

(b) a second straight line defined on the surface of the jig oriented orthogonal to the first straight line, for alignment with one of the shorter sides of the test plate while simultaneously aligning the first straight line with the first longer side of the test plate, so the jig will be positioned such that the first line may be cut almost through the center of the test plate;

(c) a third straight line defined on the surface of the jig oriented at a predetermined angle relative to a first longer side of the jig for alignment with the first line cut through the test plate, for positioning the jig such that a second line may be cut through the test plate in alignment with the first longer side of the jig and intersecting the first line cut through the jig at a predetermined angle relative thereto;

(d) an opening interposed in the middle of the first straight line and extending through the jig for alignment of the first straight line with the first longer side of the test plate to orient the jig for cutting the first line on the test plate; and (e) the first, second and third straight lines and the opening being so positioned that the intersection of the first and second lines cut in the test plate is disposed almost in the center of the test plate and the cuts uniformly extend from the intersection in four directions.

Preferably, the above-mentioned predetermined angles may be 30° or 60° as can be used for the cross-cuts in the salt spray test.

According to the present invention, the jig may have two of the first, second and third straight lines defined on the surface of the jig. This configuration permits the jig to be used for two types of cross-cuts, with the most preferable combination providing the capability to make intersecting cross-cut lines at predetermined angles of 30° and 60°.

Preferably, a scale is defined on at least one of the first and opposite longer sides of the jig. In this case, one end of the third straight line terminates at the mid-point of the scale on the first longer side of the jig, a fourth straight line defined on the surface of the jig intersects the opposite end of the third straight line, and another opening is interposed at the intersection of the third and fourth straight lines and extends through the jig. The opening and intersection of the third and fourth straight lines is used to align the third straight line with the first line cut through the test plate so that the jig may be positioned so that the second line cut through the test plate may be cut almost through the center thereof. Preferably, the scale is marked in 5 mm increments from the above-mentioned mid-point.

It is also preferable that the jig according to the present invention further comprises slits for making cuts in a cross-cut adhesion test. In this case, the slits may be disposed at increments of either 1 m/m or 2 m/m, or at intervals of both 1 m/m and 2 m/m.

According to the present invention, the first and second straight lines of the jig are adjusted to predetermined sides of a test plate to draw a line on the test plate in alignment with the longer side of the jig, and then, a third straight line is adjusted to the first drawn line to draw a line on the test plate in alignment with the longer side of the jig, whereby intersect lines at a predetermined angle can be obtained on the test plate.

Accordingly, it is an object of the present invention to provide a jig for a cross hatching test which can easily make cross-cuts in the center portion of a test plate with good reproducibility.

While there will be illustrated and described what is at present considered to be preferred embodiments of the present invention, it is intended that the present invention not be limited to the particular embodiments disclosed as the best mode.

BRIEF DESCRIPTION OF THE DRAWINGS

FIGS. 2 to 4 are views for explaining modes in using the jig in FIG. 1;

DETAILED DESCRIPTION OF THE PREFERRED EMBODIMENTS

Embodiment 1

Figure 1:
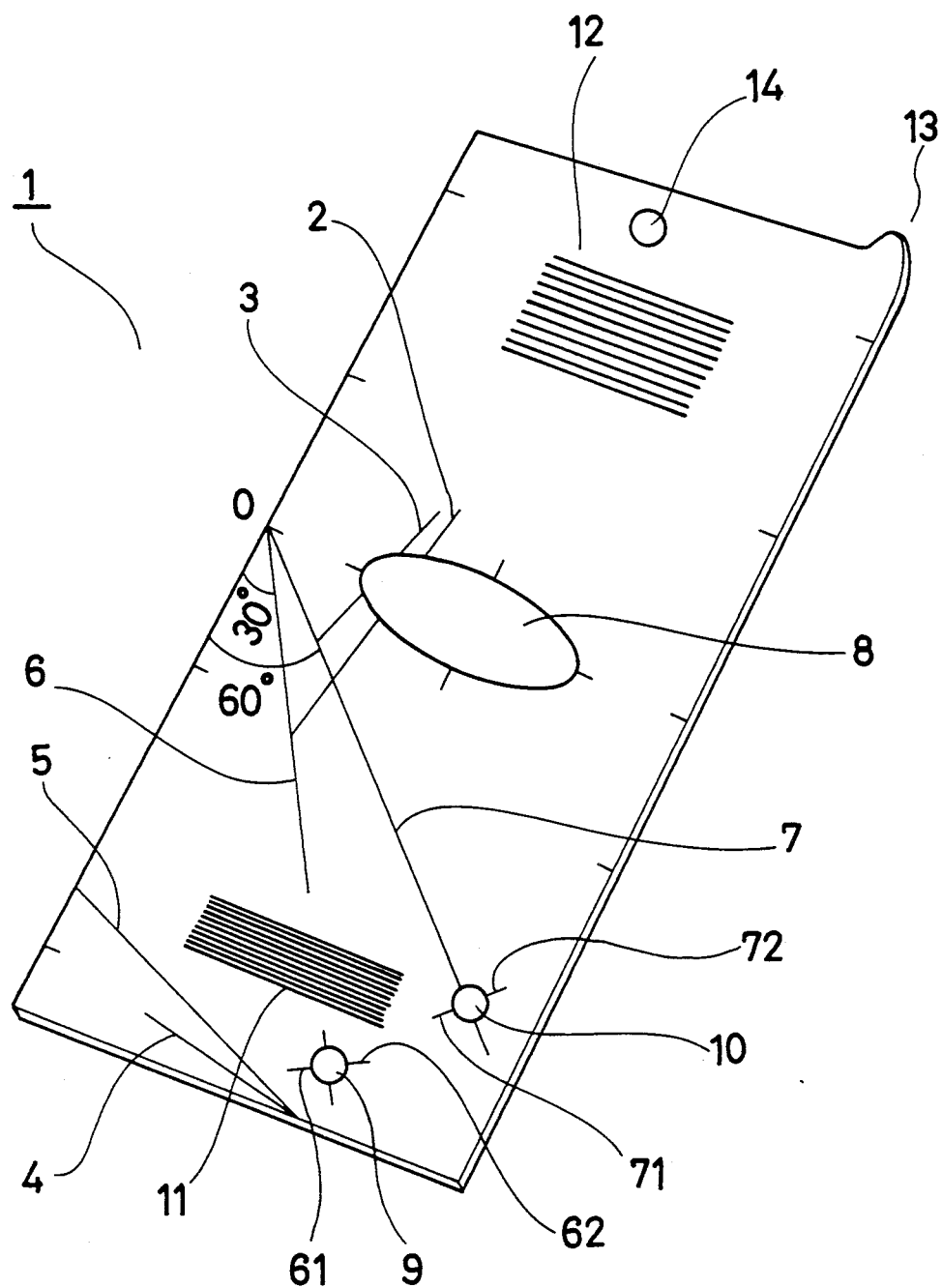
FIG. 1 is a perspective view showing an embodiment of a jig for a cross hatching test according to the present invention.

FIG. 1 is a perspective view showing an embodiment of a jig for a cross hatching test according to the present invention. Referring to FIG. 1, a jig 1 is formed of a stainless thin plate which is 2 m/m in thickness, 150×70 m/m in dimensions and rectangular in shape. The jig 1 is provided with prescribed lines and openings, as shown in FIG. 1 and described below.

Line 2 is a first guide line (a first straight line) adjusted to the left longer side of a test plate (stated below) for 30° cross, a line 3 is another first guide line (another first straight line) for 60° cross, a line 4 is a second guide line (a second straight line) orthogonal to the line 2 and adjusted to the lower shorter side of the test plate for 30° cross, a line 5 is another second guide line (another second straight line) orthogonal to the line 3 and adjusted to the lower shorter side of the test plate for 60° cross, a line 6 is a third guide line (a third straight line) provided with an angle of 30° to the left longer side of the jig for 30° cross, a line 7 is another third guide line (another third straight line) provided with an angle of 60° to the left longer side of the jig for 60° cross, opening 8 is a hole interposed in the lines 2 and 3 to accurately align lines 2 or 3 with the left longer side of the test plate opening 9 is an end point hole for 30° cross, and opening 10 is another end point hole for 60° cross.

Lines 6 and 7 terminate at the mid-point of the left longer side of the jig 1 and correspond to the initial point 0.

The jig is marked with scales on its left and right longer sides for defining a line-drawn section. The scales are marked at the mid-point on both of the longer sides and in 30 m/m increments from the respective mid-points along the sides.

Opening 8 is located so that the center of the opening corresponds with the center of jig 1. In order to easily identify the center of the jig 1, opening 8 is marked with scales at 90° increments.

The center of opening 9 is located 60 m/m from point 0 on line 6. Line 61—62 is provided as a fourth straight line in order to find the center position of opening 9.

The center of opening 10 is located 60 m/m from point 0 on line 7. Line 71—72 is provided as another fourth straight line in order to find the center position of opening 10.

The jig 1 further comprises slits 11 for cuts at 1 m/m intervals, and slits 12 for cuts at 2 m/m intervals, for the cross-cut adhesive test.

Reference numerals 12 and 14 denote a pick-up flap and an opening at which the jig 1 may be hung up.

Use of the jig 1 for a cross hatching test, employing a 60° cross-cut test, is described below in connection with FIGS. 2 to 4.

(1) As shown in FIG. 2, using the opening 8, the first (left) longer side of a test plate T is aligned with line 3 as the first straight line on the jig 1, while the lower shorter side of the test plate T is aligned with line 5 as the second straight line on the jig 1. Keeping the test plate and the jig in this position, the test plate T is cut straight along the guide of the opposite (right) longer side of the jig 1 extending from mark U to mark V (120 m/m).

Removing the jig 1, the test plate T has a cut almost passing through its center, as shown in FIG. 3.

(2) As shown in FIG. 4, the straight cut on the test plate T is aligned with line 7 as the third straight line so that the lower end point of the straight cut on the test plate is in the opening 10. This is accomplished by aligning the lower end point of the straight cut with the fourth line designated in FIG. 4 as Line 71—72. Keeping the test plate and the jig in this position, the test plate T is cut straight along the guide of the longer side of the jig 1 extending from mark W to Mark X (120 m/m).

In this way, a 60 cross-cut is obtained with an intersection positioned almost in the center of the test plate T and with cuts uniformly extending from the intersection in four directions.

While the explanation is omitted, a 30 cross-cut can be easily attained by using lines 2, 4 and 6 in the above described manner.

Embodiment 2

Figure 5:
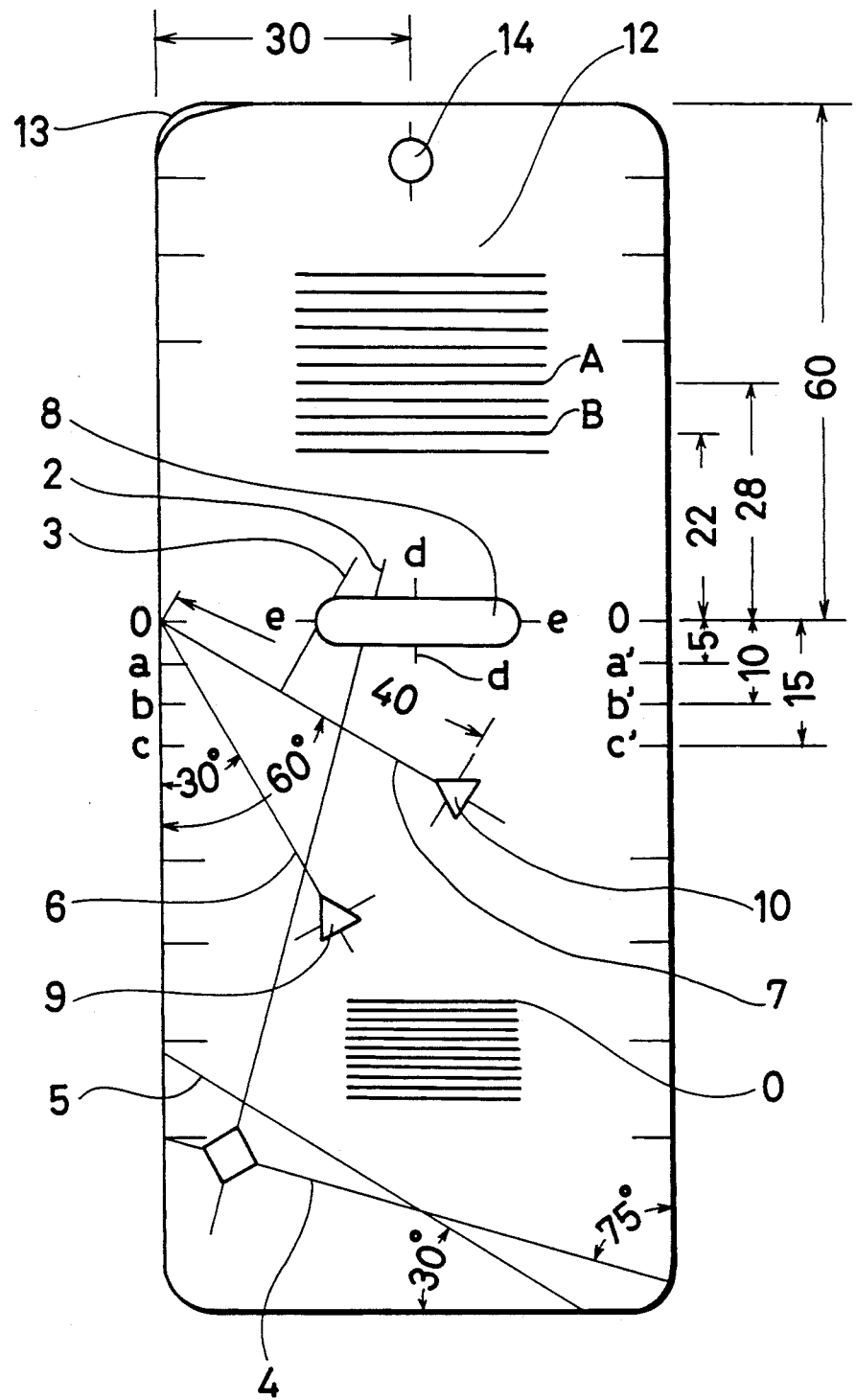
FIG. 5 is a perspective view showing another embodiment of the jig for a cross hatching test according to the present invention.

FIG. 5 is a plan view showing the structure of another embodiment of the jig according to the present invention. The jig is made of a steel plate coated with Teflon and 140×60 m/m in size, comprising lines and openings of predetermined dimensions and shapes as shown in FIG. 5. Corresponding components indicated by like reference numerals in FIGS. 1 and 5 have the same features, but note that point 0 is positioned a predetermined distance off the middle point of a longer side.

Also, the right and left longer sides of the jig are provided with marks a, a', b, b' and c, c' at positions 5, 10 and 15 mm, respectively, from the marks of point 0 on the right and left longer sides. Marks d, e are used to locate the center of opening 8.

The following will explain and describe how a cross-cut adhesion test may be applied at 5 mm increments in the center portion of a test plate (150×70 m/m) with the jig formed with the above-mentioned embodiment.

Figure 6:
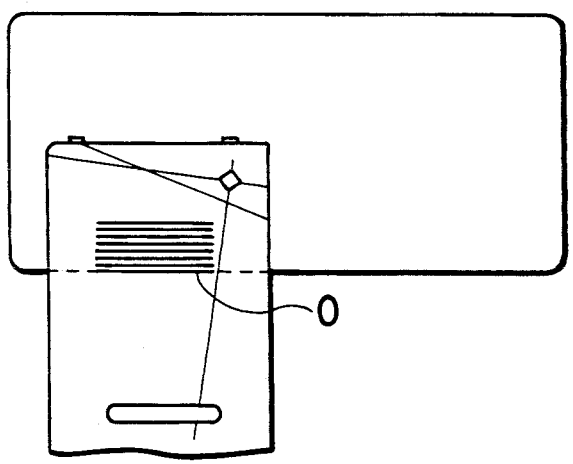
FIGS. 6 to 10 are views for explaining modes in using the jig in FIG. 5.

The jig is set on the test plate with a longer side (150 mm) of the test plate adjusted as shown in FIG. 6. Then, a slit 0 which is closest to opening 8 is aligned with the lower longer side of the test plate. With the jig and test plate in this position, two or more marks are made on the test plate along the edge of the top (shorter) side of the jig. Using a longer side of the jig, the jig is aligned with the two or more marks which were placed on the test plate. With the jig and test plate in this position, a line (center line) is drawn on the test plate along the long side of the jig.

Figure 7:
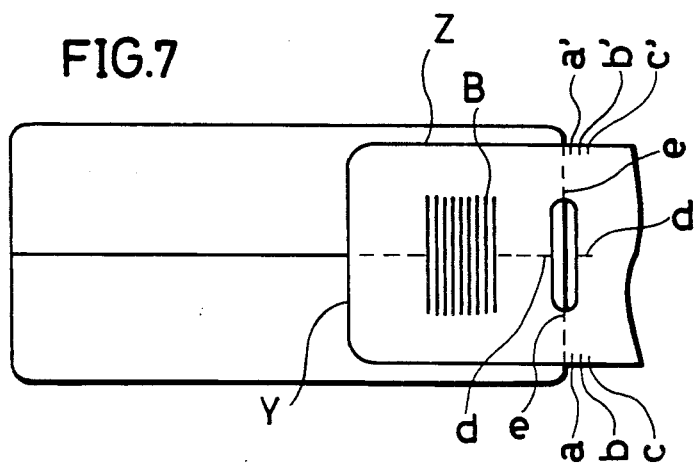
Figure 8:
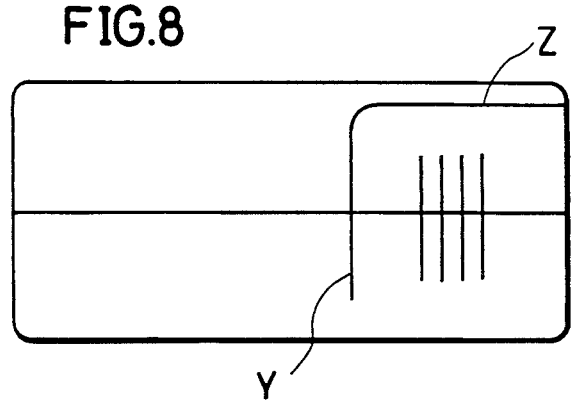

Then, as shown in FIG. 7, mark "d" of opening 8 is aligned with the center line of the test plate, while mark "e" of opening 8 is aligned with the shorter (right) side of the test plate. A curved line is then drawn, continuously along the top longer side of the jig and the left shorter side of the jig, on the test plate. Thereafter, keeping the test plate and jig in the same position, the test plate is cut along a slit B in slits disposed at 2 mm. Then, instead of line e—e, lines a—a', b—b' and c—c' are aligned with the shorter (right) side of the test plate in this order, and upon each new alignment the test plate is cut along the slit B. Thus, as shown in FIG. 8, the test plate is cut at intervals of 5 mm.

Figure 9:
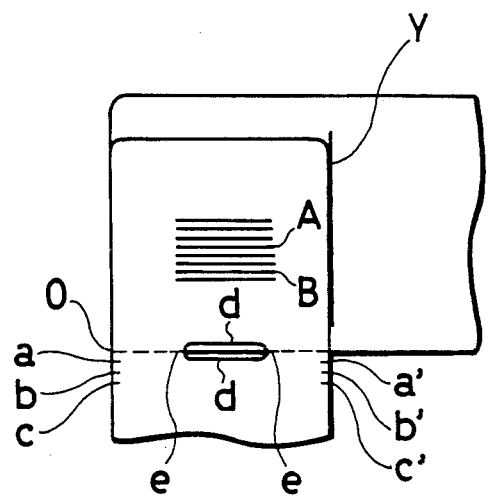
Figure 10:
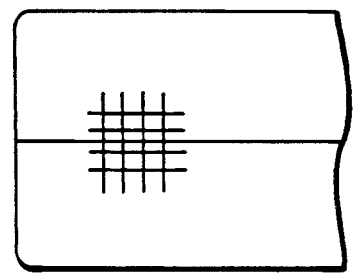

Then, as shown in FIG. 9, the right longer side of the jig is aligned with part Y of the curved line, while the line e—e of opening 8 is aligned with the longer (bottom) side of the test plate so the test plate may be cut along a slit A in slits disposed at 2 mm. Thereafter, similar to the above, lines a—a', b—b' and c—c' are aligned with the longer (bottom) side of the test plate in this order, and upon each new alignment the test plate is cut along the slit A. In this way, as shown in FIG. 10, the 5 mm cross-cut adhesion test is applied to the center portion of the test plate.

As has been described, according to the present invention, uniform cross-cuts at predetermined angles can be easily made in the center portion of a test plate with good reproducibility, and thus, a highly reliable cross-cut test can be applied.

Also, according to the present invention, marks at predetermined intervals are arbitrarily provided in a line-drawn section, so that a cross-cut adhesion test can be easily applied with cross-cuts at arbitrary intervals.

I claim:

1. A rectangularly-shaped jig used for ruling straight lines intersecting each other at a predetermined angle on a rectangular test plate for a cross hatching test, comprising:

(a) a first straight line defined on the surface of the jig for alignment with a first longer side of the test plate to orient the jig for cutting a first line on the test plate in alignment with the opposite longer side of the jig;

(b) a second straight line defined on the surface of the jig, oriented orthogonal to said first straight line, for alignment with one of the shorter sides of the test plate simultaneous with alignment of said first straight line with said first longer side of the test plate, for positioning the jig such that the first line may be cut almost through the center of the test plate;

(c) a third straight line defined on the surface of the jig oriented at said predetermined angle relative to a first longer side of the jig for alignment with the first line cut through the test plate, for positioning the jig such that a second line may be cut through the test plate in alignment with the first longer side of the jig and intersecting said first line at said predetermined angle relative thereto;

(d) an opening interposed in the middle of said first straight line and extending through the jig, for alignment of the first straight line with the first longer side of the test plate to orient the jig for cutting the first line on the test plate; and (e) said first, second and third straight lines and said opening being so positioned that the intersection of the first and second lines cut in the test plate is disposed almost in the center of the test plate and the cuts uniformly extend from the intersection in four directions.

2. A jig according to claim 1, wherein a scale is defined on at least one of the first and opposite longer sides of the jig.

3. A jig according to claim 3, wherein said third straight line terminates at one end at the mid-point of said scale on the first, longer side of the jig, and further comprising:

(f) a fourth straight line defined on the surface of the jig and intersecting the opposite end of said third straight line; and (g) another opening interposed at the intersection of said third and fourth straight lines and extending through the jig, for aligning said third straight line with the first line cut through the test plate so that the jig may be positioned so that the second line cut through the test plate may be cut almost through the center thereof.

4. A jig according to claim 1, wherein said predetermined angle at the intersection is 30°.

5. A jig according to claim 1, wherein said predetermined angle at the intersection is 60°.

6. A jig according to claim 1, wherein there are provided two of said first, second and third straight lines, respectively, and said predetermined angle is 30° or 60°.

7. A jig according to claim 1, further comprising slits for making cuts in a cross-cut adhesion test.

* * * * *